United States Patent [19]

Franklin

[11] Patent Number: Plant 6,361

[45] Date of Patent: Nov. 1, 1988

[54] APPLE TREE—FRANKAD CULTIVAR

[75] Inventor: Henry E. Franklin, Stanthorpe, Australia

[73] Assignee: Stark Brothers Nurseries and Orchards Company, Louisiana, Mo.

[21] Appl. No.: 923,175

[22] Filed: Oct. 27, 1986

[51] Int. Cl.[4] ..... A01H 5/03
[52] U.S. Cl. ..... Plt./34
[58] Field of Search ..... Plt. 34

*Primary Examiner*—Robert E. Bagwill

*Attorney, Agent, or Firm*—Burns, Doan, Swecker & Mathis

[57] ABSTRACT

A new and distinct apple variety is provided which is especially well adapted for growing in warmer apple growing areas because of its unusually good heat tolerance. The new variety possesses a medium large upright and spreading growth habit and abundantly forms attractive dessert-type fruit. Such fruit is tangy and richly flavored, and possesses a bright red skin coloration coupled with exceptionally good flesh firmness when compared to other early ripening apple varieties.

1 Drawing Sheet

SUMMARY OF THE INVENTION

The new variety was discovered in 1959 as an open pollinated seedling of Golden Delicious apple growing in the cultivated state in my orchard at Stanthorpe, Queensland, Australia. The seeds from the Golden Delicious fruit which produced the new variety were planted in 1950. Since a tree of the Williams Favorite variety was growing near to the Golden Delicious female parent, it is possible that the Williams Favorite variety may have been the male parent. The new variety first fruited in 1959 and was selected because of its unique combination of characteristics.

It was found that the new apple variety possessed (a) an unusually good heat tolerance, (b) a medium large upright and spreading growth habit, and (c) the consistent production of heavy crops of early ripening large round-oblate sprightly flavored fruit having a bright red skin coloration and firm flesh.

The fruit of the new variety ripens early in the season. For instance, the fruit commonly ripens during midsummer or approximately four weeks prior to the Red Delicious-Mood apple cultivar when grown at Louisiana, Pike County, Mo. When grown at other locations the disparity in ripening times may be even greater.

The flesh of the new apple variety is satiny white with a very slight greenish tinge. Such flesh is unusually firm for a early ripening apple variety and possesses a rich tangy taste.

The bright red skin coloration of the fruit is present even when warm temperatures are encountered which are commonly not favorable for the production of good fruit coloration. The fruits develop the attractive bright red coloration even when the nighttime temperatures exceed 75° F. However, the fruit coloration is somewhat darker in growing areas where cooler nights are experienced. Heavy crops of such fruit consistently are formed.

Asexual propagation of the new variety was first carried out in the Spring of 1960 at my nursery at Stanthorpe, Queensland, Australia. This and subsequent propagations have demonstrated that the characteristics of the new variety come true to form and are established and transmitted through succeeding generations.

This new variety has been named the Frankad cultivar and is subject to commercialization by Stark Brothers Nurseries and Orchards Company under the Adina trademark.

BRIEF DESCRIPTION OF THE PHOTOGRAPH

The accompanying photograph shows typical specimens of the fruit and foliage of the new variety in color as nearly true as it is reasonably possible to make the same in a color illustration of this character.

DETAILED DESCRIPTION OF THE NEW VARIETY

The following is a detailed description of the new variety where color terminology is to be accorded its ordinary dictionary significance except where otherwise indicated. The specimen described was grown at Louisiana, Pike County, Mo.

Representative dates of first and last pickings were Aug. 12, 1985 and Aug. 20, 1985 respectively.

Tree: Medium large; vigorous, upright and spreading; tall; round-topped; medium growing; hardy; productive; regular bearing.

*Trunk.*—Medium stocky; medium smooth.

*Branches.*—Medium thick; medium smooth; medium branching; grey-green in coloration. Lenticels. - medium number, medium in size.

*Leaves.*—Large; wide; long; ovate-elliptic; taper-pointed; medium thick; rugose; light pubescence on undersurface. Upper surface. Cossack Green Plate VI Color No. 33, tone m of Ridgeway Color Standards and Nomenclature. Undersurface. Cosse Green Plate V Color No. 29, tone i of Ridgeway Color Standards and Nomenclature. Length. — approximately 3 13/16 to 3⅞ inches. Width. — approximately 1⅞ to 2⅜ inches. Margin. — coarsely serrate. Petiole. — medium long (approximately 7/8 inch); medium thick.

Flowers: Medium early; large, white. Representative dates of first and full bloom were Apr. 18, 1985 and Apr. 24, 1985, respectively.

Fruit:

*Maturity when described.*—Hard ripe — Aug. 16, 1985.

*Size.*—Uniform. Axial diameter. — approximately $2\frac{3}{4}$ to $2\frac{7}{8}$ inches. Traverse in suture plane. — approximately 3 to $3\frac{1}{4}$ inches.

*Form.*—Globose-oblate, truncate at apex, slightly ribbed.

*Cavity.*—Symmetrical; rounded; undulate. Depth. — approximately 9/16 inch. Breadth. — approximately $1\frac{3}{8}$ inch. Markings. — light russet; yellowish Citrine Green Plate XVI Color No. 23, tone i of Ridgeway Color Standards and Nomenclature.

*Basin.*—Symmetrical. Depth. - approximately 3/16 inch. Breadth. — approximately 7/8 to 1 inch. Markings. — none.

*Stem.*—Medium-stout.

*Calyx.*—Open; segments persistent; broadly lanceolate. Length. — approximately 5/16 inch; separated at base; erect; reflexed from base at apex. Outer-surface. — pubescent. Inner-surface. — pubescent.

*Eye.*—Large; open.

*Skin.*—Thick; tough; smooth; glossy; waxed. Dots. conspicuous; many; large; even. Color of Dots. — white. Distribution of Dots. — all over; most numerous toward the cavity. Ground Color. — Eugenia Red Plate XIII Color No. 1′ of Ridgeway Color Standards and Nomenclature. Color of Markings. — striped; splashed; Neutral Red Plate XXXIII Color No. 71″, tone k of Ridgeway Color Standards and Nomenclature. Bloom. — abundant. Scarfskin. — white; heavy; distributed mostly toward the cavity. General Color Effect. — dark purple stripes over bright red ground color.

*Flesh.*—Juicy. Color. — satiny white with greenish tinge. Texture. — firm; tender; coarse; crisp.

Flavor. — sub-acid; sprightly rich. Aroma. — pronounced. Quality. — good.

*Cor.*—Sessile. Bundle Area. — large; cordate; symmetrical; halves of area equal. Core Lines. — clasping; in cross-section distinct; Carpellary Area. — distinct; large. Calyx Tube. — glabrous toward base; funnel-form. Stem of Funnel. — long. Depth of Calyx Tube to Shoulder. — approximately 9/16 inch. Entire Depth. — approximately $\frac{3}{4}$ inch. Styles. — present; united toward base; pubescent throughout. Stamens. — one distinct whorl; median. Auxillary Cavity. — present. Seed Cells. — abasile; open. Cell Walls.— thin; tough. Length. — approximately $\frac{7}{8}$ inch. Bredth. — approximately $1\frac{1}{8}$ inch. Longitudinal Section. — oblate; emarginate. Surface. — fissured. Cross-section. — narrow.

*Seeds.*—Number perfect — 10; number imperfect 0. Number in One Cell. — 2 Length. — approximately 5/16 inch. Breadth. — approximately 3/16 inch. Form. — obtuse. Color. — brown.

Use: Market, dessert.

Keeping quality: Good, stores well.

Resistance to:

*Insects.*—Medium.

*Diseases.*—Medium.

I claim:

1. A new and distinct variety of apple tree, substantially as illustrated and described, characterized by (a) an unusually good heat tolerance, (b) a medium large upright and spreading growth habit, and (c) the consistent production of heavy crops of early ripening large round-oblate sprightly flavored fruit having a bright red skin coloration and firm flesh.

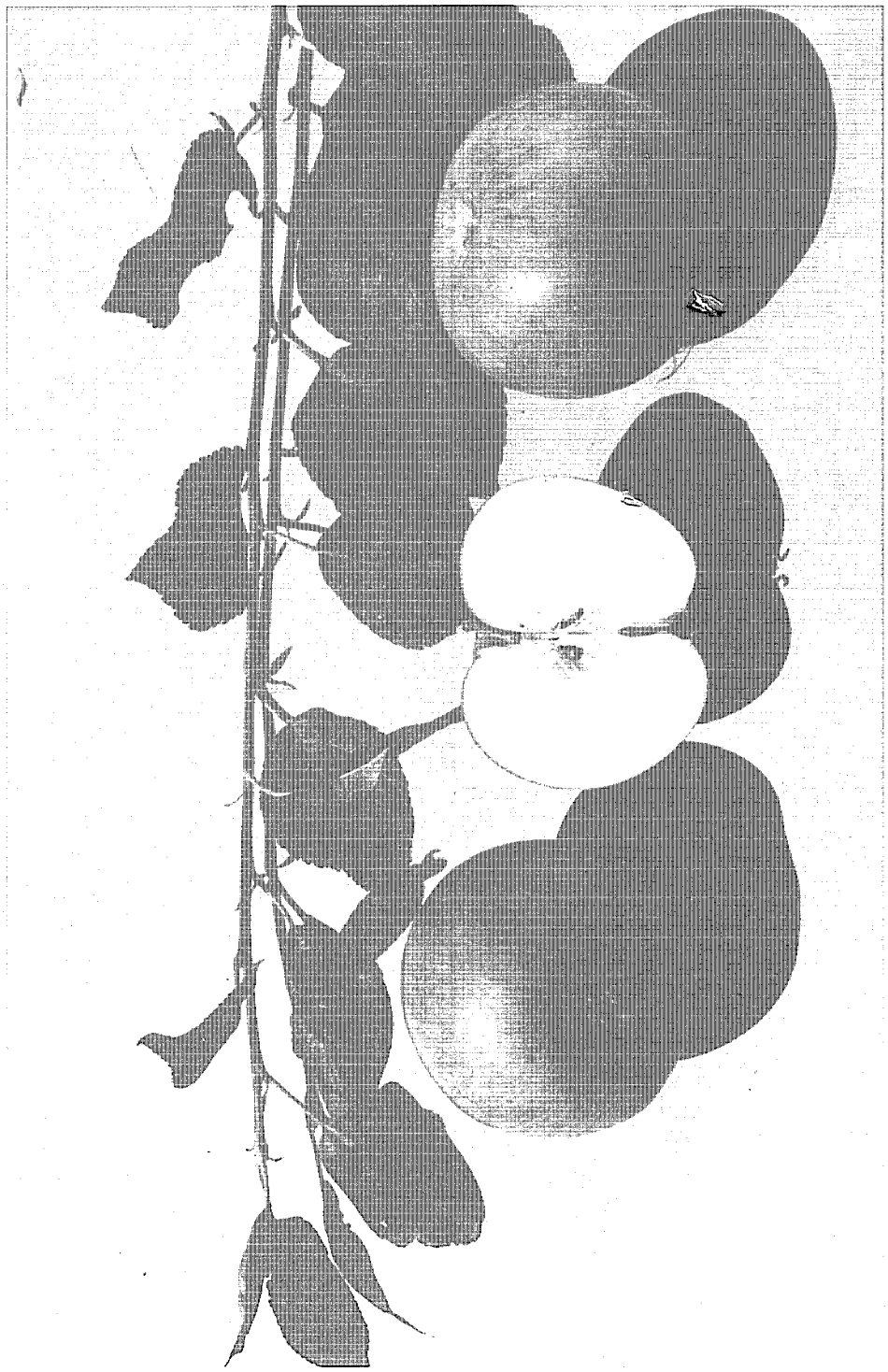

* * * * *